US006248577B1

(12) United States Patent
Vasanthakumar et al.

(10) Patent No.: US 6,248,577 B1
(45) Date of Patent: Jun. 19, 2001

(54) HYPOXANTHINE-GUANINE PHOSPHORIBOSYL TRANSFERASE

(75) Inventors: Geetha Vasanthakumar, Vestavia Hills; John A. Montgomery, Birmingham, both of AL (US)

(73) Assignee: Southern Research Institute, Birmingham, AL (US)

( * ) Notice: Subject to any disclaimer, the term of this patent is extended or adjusted under 35 U.S.C. 154(b) by 0 days.

(21) Appl. No.: 07/552,744

(22) Filed: Jul. 16, 1990

(51) Int. Cl.[7] .............................. C12N 15/54; C12N 9/12; C12N 15/70

(52) U.S. Cl. ..................... 435/193; 435/69.1; 435/194; 435/252.33; 435/320.1; 536/23.2

(58) Field of Search ................................ 435/69.1, 172.3, 435/183, 194, 320.1, 252.33; 536/23.2

(56) References Cited

PUBLICATIONS

King, A., et al, 1987, Nucleic Acids Research 15(24): 10469–10481.*
Marsh, P., 1986, Nucleic Acids Research 14(8): 3603.*
Kalle, G., et al., 1961, Biochimica et Biophysica Acta 53: 166–173.*
McIntyre, P., et al., 1987, International Journal of Parasitology 17(1): 59–68.*
Remy, C.N., et al., (1957) Journal of Biological Chemistry 228: 325–338.*
Vasantha Kumar, G., et al., 1989, Nucleic Acids Research, 17(20): 8382.*
Dayhoff, M.O., Ed., 1970 Atlas of Protein Sequence and Structure, vol. 5, pp. 101–110, (Barlow & Dayhoff) Nat'l. Biomedical Research Foundation.*
Smith, D.B., et al., 1988, Molecular and Boichemical Parasitology 27: 249–246.*
Sheppard, H.W., et al., 1986, Molecular and Biochemical Parasitology 19: 35–43.*
Vasanthakumar, G., et al., 1989, The Journal of Cellular Biochemistry, Supplement E, p. 125, Abstract 0 485.*
Craig, S.P., et al., 1988, Nucleic Acids Research, 16(14): 7087–7100.*
Fujimori. S., et al., 1988, Human Genetics, 79: 39–43.*
Fenwick, R.G., et al., 1984, Somatic Cell and Molecular Genetics, 10(1): 71–84.*
Singh, G., et al., 1988, Cancer Chemo Therapy and Pharmacology, 22: 191–196.*
Enea, V., et al., 1984, "DNA cloning of Plasmodium falciparum circumsporozoite gene: amino acid sequence of repetitive epitope", vol. 225, pp. 628–630.*
Hyde, J. E., et al., 1984, "Characterization and translation studies of messenger RNA from the human malaria parasite Plasmodium falciparum and construction of a cDNA library"; Molecular and Biochemical Parasitology, vol. 10, pp. 269–285.*
Sullivan, M. A., et al., 1987, "Isolation and characterization of the gene encoding hypoxanthine–guanine phosphoribosyltransferase from Plasmodium falciparum", in Molecular Strategiesof Parasitic Invasion, Agabian, N., et al., Eds., pp. 575–584.*
Shahabuddin, M., et al., 1990, "The gene for hypoxanthine phosphoribosyltransferase of Plasmodium falciparum complements a bacterial HPT mutation", Molcular and Biochemical Parasitology, vol. 41, pp. 281–288.*

(List continued on next page.)

*Primary Examiner*—Ponnathapuachuta Murthy
*Assistant Examiner*—William W. Moore
(74) *Attorney, Agent, or Firm*—Needle & Rosenberg, P.C.

(57) ABSTRACT

The present invention describes the previously unreported cloning and isolation of HGPRT cDNA containing an open reading frame corresponding to the HGPRT of *Plasmodium falciparum*, present the complete nucleotide sequence of the *Plasmodium falciparum* HGPRT DraI/PstI cDNA fragment, and the expression of this gene product in an *E. coli* strain deficient in purine salvage.

7 Claims, 3 Drawing Sheets

OTHER PUBLICATIONS

Figure 1:
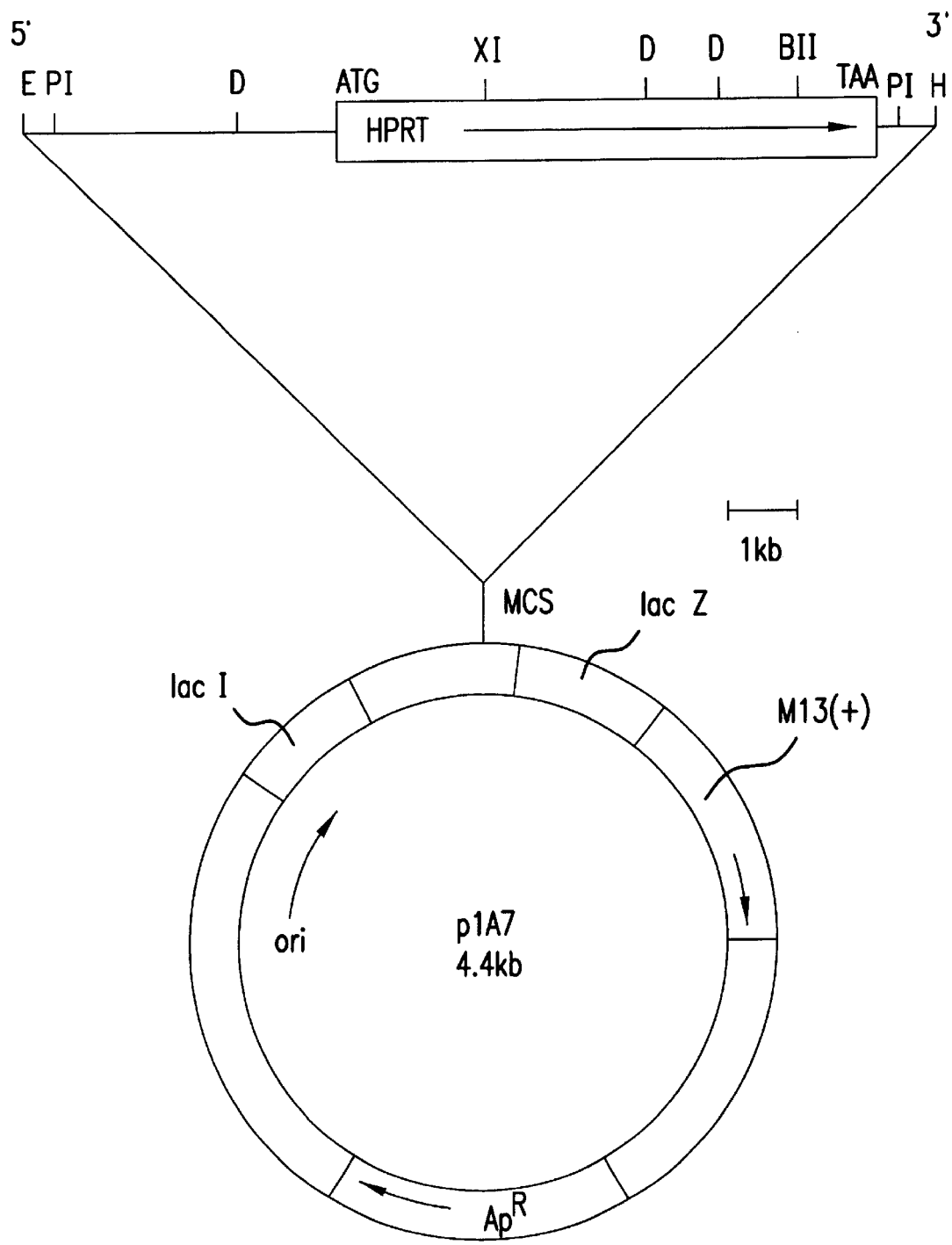

Cappai, R., et al., 1992, "The Plasmodium falciparum hypoxanthine–guanine gene has phosphoribosyltransferase phosphoribosyltransferase gene has a 5' upstream intorn", Molecular and Biochemical Parasitology, vol. 54, pp. 117–120.*

Allen, T. E., et al., 1993, "Cloning and expression of the hypoxanthine–guanine phosphoribosyltransferase gene from Trypanosoma brucei", Nucleic Acids Research, vol. 21, pp. 5431–5438.*

Allen, T. E., et al., 1994, "Molecular characterization and overexpression of the hypoxanthine–guanine phosphoribosyltransferase gene from Trypanosoma cruzii", Molecular and Biochemical Parasitology, vol. 65, pp. 233–245.*

Keough, D. T., et al., 1998, "Expression and properties of recombinant P. falciparum hypoxanthine–guanine phosphoribosyltransferase", in Purine and Pyrimidine Metabolism in Man IX, Griesmacher et al., Eds., Plenum Press, pp. 735–739.*

Keough, D. T., et al., 1999, "Purfication and characterization of Plasmodium falciparum hypoxanthine–guanine phosphoribosyltransferase and comparison with the human enzyme", Molecular and Biochemical Parasitology, vol. 98, pp. 735–739.*

Balaram, H., et al., 1999, "Tinkering with enzymes", Journal of the Indian Institute for Science, vol. 79, pp. 49–60.*

* cited by examiner

HYPOXANTHINE-GUANINE PHOSPHORIBOSYL TRANSFERASE

The control of malaria has proved elusive, and an estimated 60 million cases of the disease occur worldwide each year. Malaria is now on the increase throughout the tropics, especially in the Indian subcontinent. In 1984, 1,016 cases of malaria were reported in the United States and of these, 26 percent were caused by *Plasmodium falciparum*, the most lethal of the four malarial parasites which infect humans.

The disease caused by *Plasmodium falciparum* differs from that caused by the other forms in a number of important respects, largely by the capacity of this species of protozoa to obstruct microcirculation in various organs and the high intensity—many times the number of parasitized red blood cells number in excess of 10 percent—of parasitemia.

*Plasmodium falciparum* undergoes three cycles of development in its vertabrate host and elicits stage-specific immune responses. This stage-specific aspect of the immune response has made it difficult to isolate antigens that would be useful in developing a vaccine against malaria. Thus, the infection is currently being treated by combination chemotherapy.

Recent increases in the frequency of chloroquine and pyrimethamine resistant malarial infections, specifically infection with *P. falciparum*, have emphasized the urgent need for development of new chemotherapeutic agents to combat this disease. However, a more efficient and rational approach to the development of chemotherapeutic agents is to exploit defined differences in host and parasite metabolism. These differences can then become the basis upon which inhibitors specific to parasite enzymes may be developed and utilized as specific agents in the therapeutic treatment of the infection.

The choice of a potential target enzyme for malarial parasites is suggested, under the approach taken by the present invention, by the inability of the parasite to synthesize purines de novo during the intra-erythoocytic stages of their life cycle in their mammalian host. The parasite therefore relies upon the host to provide the necessary free pre-formed purines to satisfy its requirement. One important enzyme involved in the salvage of purines from Plasmodium-infected red blood cells is hypoxanthine-guanine phosphoribosyltransferase (HGPRT). HGPRT is a tetrameric enzyme in man which catalyzes the phosphoribosylation of hypoxanthine and guanine to form inosine monophosphate and guanosine monophosphate, in the presence of 5'-phosphoribosyl-1-pyrophosphate. In Plasmodium, the enzyme appears as a dimer with a weight of 52 kD.

The activity of this enzyme is present in *P. falciparum* blood stage parasites at high levels, and prior experimentation [see Microbiological Reviews 43(4): 453 (1979)] with Plasmodium sp. has indicated that the salvage of hypoxanthine is an essential key element in parasitic nucleic acid synthesis as the only significant source of purines. A better understanding of the essential nature of the HGPRT enzyme in the purine nucleotide salvage in *Plasmodium falciparum* can be had with an examination of the following schematic pathway indicating the salvage pathways in this organism:

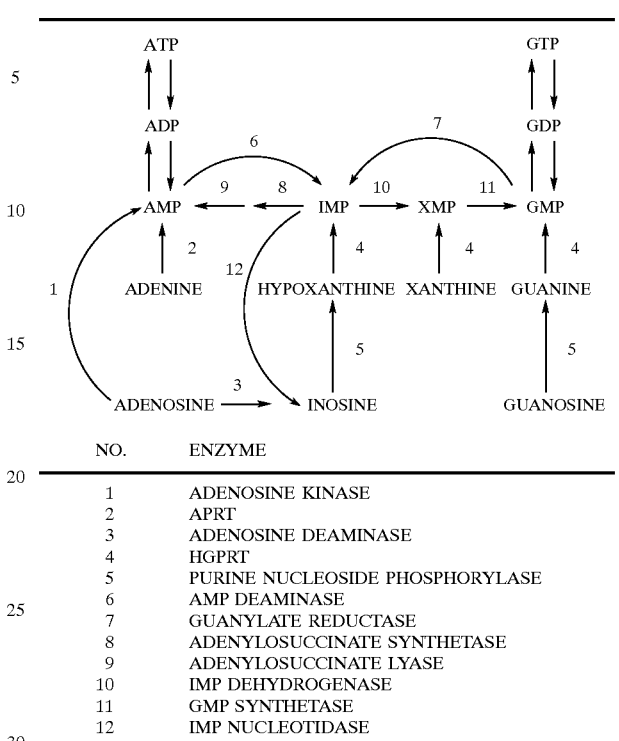

| NO. | ENZYME |
|-----|--------|
| 1 | ADENOSINE KINASE |
| 2 | APRT |
| 3 | ADENOSINE DEAMINASE |
| 4 | HGPRT |
| 5 | PURINE NUCLEOSIDE PHOSPHORYLASE |
| 6 | AMP DEAMINASE |
| 7 | GUANYLATE REDUCTASE |
| 8 | ADENYLOSUCCINATE SYNTHETASE |
| 9 | ADENYLOSUCCINATE LYASE |
| 10 | IMP DEHYDROGENASE |
| 11 | GMP SYNTHETASE |
| 12 | IMP NUCLEOTIDASE |

As can be understood from this examination, the reliance that the parasite has on its own HGPRT activity during its intra-erythrocytic stages makes this enzyme a potential target for potential therapeutic activity in the treatment of malarial disease. If HGPRT can be inhibited or removed from the parasite's purine nucleotide salvage pathway, the parasite will become, effectively, weakened to an extent wherein chemotherapeutic agents or the host's own immune responses will be able to more efficiently combat the infection.

Accordingly, it is the purpose of the present invention to describe the cloning and isolation of HGPRT cDNA containing an open reading frame corresponding to the HGPRT of *Plasmodium falciparum*, present the complete nucleotide sequence of the *Plasmodium falciparum* HGPRT DraI/PstI cDNA fragment, and demonstrate the expression of this gene product in an *E. coli* strain deficient in purine salvage.

Figure 2A:
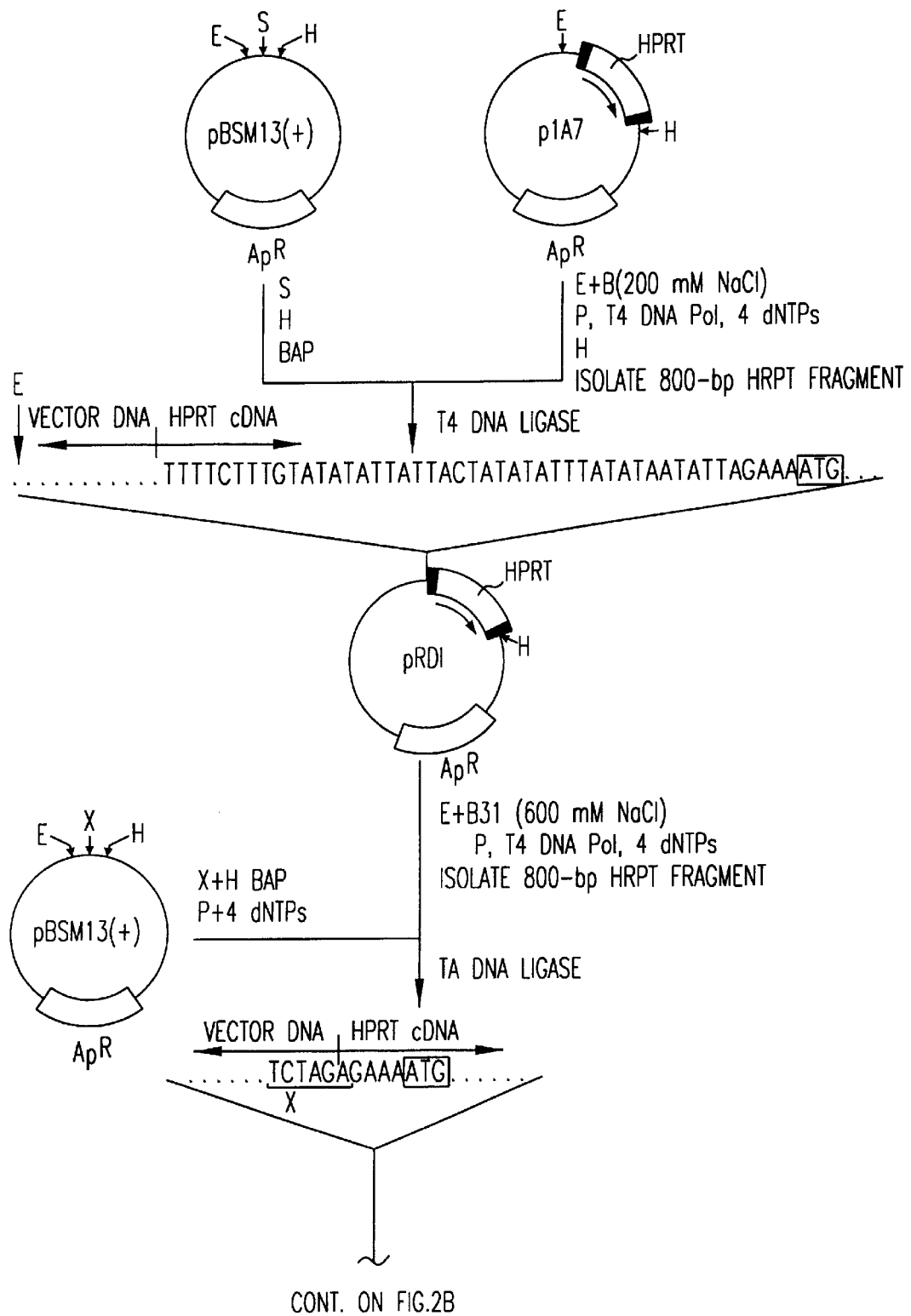
Figure 2B:
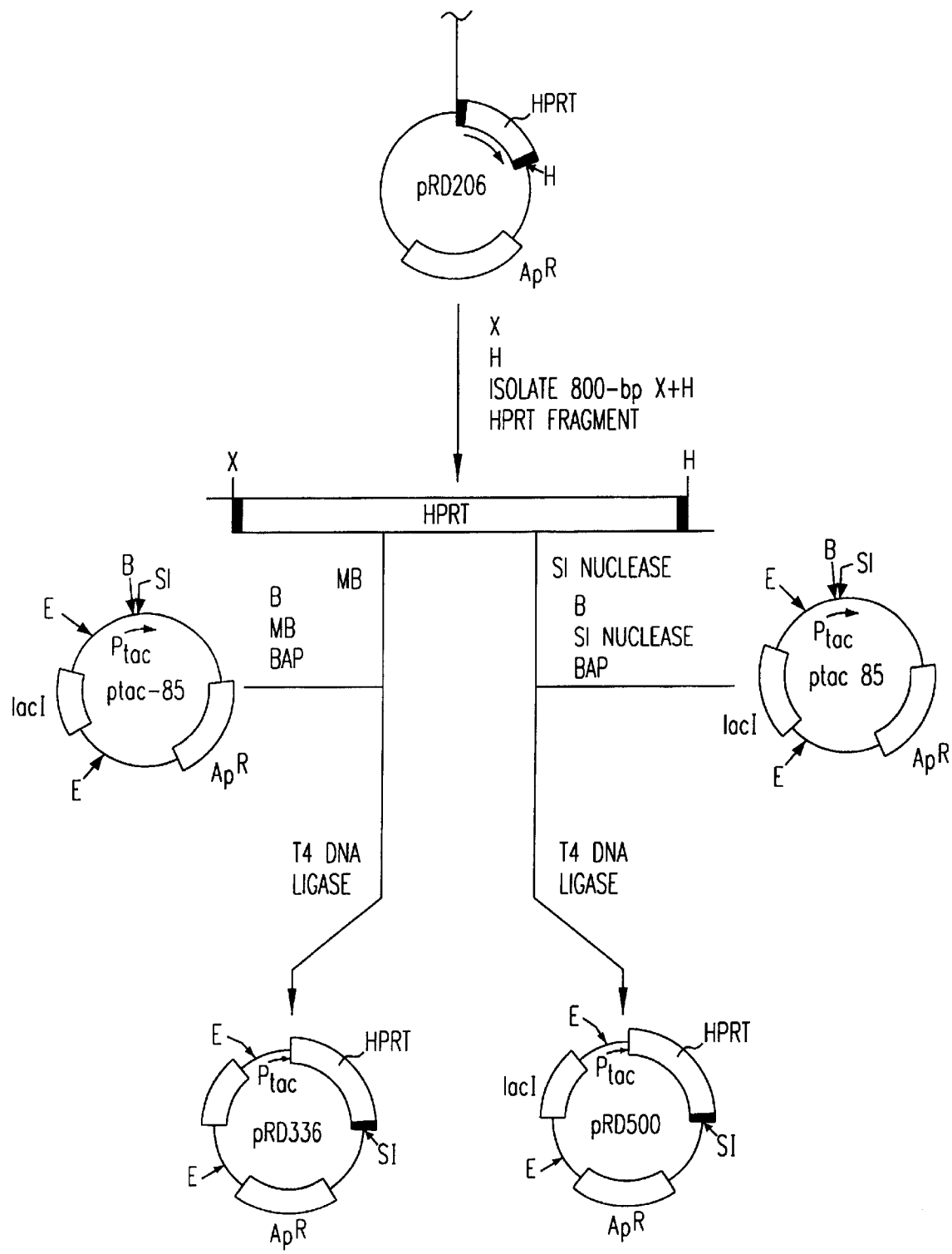

These and other aspects and purposes of the present invention will become more apparent from the following detailed description and figures. In the figures, FIG. 1 is a representation of the plasmid that contains the *P. falciparum* HGPRT cDNA according to the present invention; and FIG. 2 is a schematic representation of the construction of subclones pRD$_{336}$ and pRD$_{500}$ according to the present invention.

Sullivan and his co-workers previously isolated a partial genomic clone from a *P. falciparum* (strain 7G8) genomic library [see Science 225:625–628 (1984); or UCLA Symposia on Molecular and Cellular Biology, Alan R. Liss, Inc., New York, vol 42, pg 575 et seq. (1987)]. In Sullivan, however, a genomic clone was isolated that could encode a 194 amino acid residue polypeptide that exhibited approximately 49 percent homology to mammalian HGPRT. However, the *P. falciparum* genomic clone according to the present invention does not contain sequences that correspond to the first 29 amino acids of the mammalian HGPRT and the translation initiation codon is also absent. Furthermore, the Sullivan-isolated enzyme contained a UAG translation termination codon at the 5' end of the sequence which was in-frame with his putative *P. falciparum* HGPRT sequence.

EXAMPLE 1

Isolation of *Plasmodium falciparum* HGPRT cDNA

In order to isolate the complete cDNA of the parasite HGPRT, a cDNA library [see Science, 227:1593 (1985)] of *P. falciparum* (FCR-3, Gambia) was plated and incubated at 37° C. for 10 hr. Replicates of the plates were transferred to nitrocellulose paper and hybridized with the ($^{32}$P)-phosphate labeled genomic DNA [see UCLA Symposia, supra]. DNA on the filters was hybridized at 50° C. for 16 hr in 5X SSPE (1X SSPE is 0.18 M NaCl, 0.01 M sodium phosphate, 0.1 mM EDTA, pH 7.4), 1X Denhardt's and 100 µg/ml denatured herring sperm DNA. After hybridization, the filters were washed several times at room temperature in 2X SSPE, 0.1% SDS, and one of the isolates (p1A7) was selected for further characterization. A partial restriction endonuclease map of the 1250 bp cDNA fragment that was ligated into the Pst1 site of plasmid vector Bluescribe M13+ is shown in FIG. 1. Also shown is the proposed location and orientation of the HGPRT structural gene according to the present invention. This cDNA contains nearly 500 bp of untranslated sequence located at the upstream of the start of the this HGPRT structural gene.

The DNA sequence of the HGPRT cDNA prepared in in accordance with Example 1 was determined using the dideoxy chain termination method of Sanger [see Proc. Natl. Acad. Sci. USA 74:5463 (1977)], utilizing the Klenow fragment of DNA polymerase I (available from Boehringer-Mannheim Corporation), M13 universal and reverse primers (available from International Biotechnologies, Inc.) and alpha-$^{35}$S dATP (available from Amersham). Determination of the complete nucleotide sequence of the HGPRT cDNA according to the present invention was facilitated by sub-cloning fragments within the open reading frame into the Bluescribe plasmid vector pBS+ (available from Stratagene). DNA sequences were analyzed using known programs [see Nucl. Acids Res. 12:643 (1984)].

The nucleotide sequence of the *Plasmodium falciparum* cDNA is indicated below. This sequence differs from that published by King and his co-workers [see Nucl. Acids Res. 15:10469 (1987)] at position 427, and in addition, the expression of the protein product of the previously reported cDNA was not successful. The sequence depicted below contains a long open reading frame that can encode a polypeptide of 231 amino acid residues with a calculated molecular weight of 26,360. The cDNA according to the present invention has been successfully expressed in *E. coli*. In this sequence, the HGPRT gene cloned into pRD500 has been underlined.

```
AAAATTTATA CAAATTTTAA TATAAACTTT CACCACACCA

AAAACCCCCC ATATATATTT AATTCATAAT ATTAAAGAAA

ATATATTTTT CTTTGTATAT ATTATTACTA TATATTTATA
                 1
TAATATTGA AA    ATG CCA ATA CCA AAT AAT CCA GGA

GCT GGT GAA AAT GCC TTT GAT CCC GTT TTC GTA AAG

GAT GAC GAT GGT TAT GAC CTT GAT TCT TTT ATG ATC
```

-continued

```
CCT GCA CAT TAT AAA AAA TAT CTT ACC AAG GTC TTA

GTT CCA AAT GGT GTC ATA AAA AAC CGT ATT GAG AAA

TTG GCT TAT GAT ATT AAA AAG GTG TAC AAC AAT GAA

GAG TTT CAT ATT CTT TGT TTG TTG AAA GGT TCT CGT

GGT TTT TTC ACT GCT CTC TTA AAG CAT TTA AGT AGA

ATA CAT AAT TAT AGT GCC GTT GAG ACG TCC AAA CCA

TTA TTT GGA GAA CAC TAC GTA CGT GTG AAA TCC TAT

TGT AAT GAC CAA TCA ACA GGT ACA TTA GAA ATT GTA

AGT GAA GAT TTA TCT TGT TTA AAA GGA AAA CAT GTA

TTA ATT GTT GAA GAT ATT ATT GAT ACT GGT AAA ACA

TTA GTA AAG TTT TGT GAA TAC TTA AAG AAA TTT GAA

ATA AAA ACC GTT GCC ATC GCT TGT CTT TTT ATT AAA

AGA ACA CCT TTG TGG AAT GGT TTT AAA GCT GAT TTC

GTT GGA TTC TCA ATT CCT GAT CAC TTT GTT GTT GGT

TAT AGT TTA GAC TAT AAT GAA ATT TTC AGA GAT CTT

GAC CAT TGT TGT TTG GTT AAT GAT GAG GGA AAA AAG

AAA TAT AAA GCA ACT TCA TTA TAA    ATACATTTAT

TGAAGTGATC AAAAATGTCA CAACCTTTCT ATTTATATCA

ATTTACCCCC CCCCCCCCCC CCCCTGCAGG
```

This nucleotide sequence, and any deletions, insertions or additions which may be made within the sequence without substantially altering the expression of HGPRT enzyme, is within the scope and protection of the present invention.

This sequence encodes for the 231 amino acid residue protein, according to the present invention, of the following sequence:

Met Pro Ile Pro Asn Asn Pro Gly Ala Gly Glu Asn

Ala Phe Asp Pro Val Phe Val Lys Asp Asp Asp Gly

Tyr Asp Leu Asp Ser Phe Met Ile Pro Ala His Tyr

Lys Lys Tyr Leu Thr Lys Val Leu Val Pro Asn Gly

Val Ile Lys Asn Arg Ile Glu Lys Leu Ala Tyr Asp

Ile Lys Lys Val Tyr Asn Asn Glu Glu Phe His Ile

Leu Cys Leu Leu Lys Gly Ser Arg Gly Phe Phe Thr

Ala Leu Leu Lys His Leu Ser Arg Ile His Asn Tyr

Ser Ala Val Glu Thr Ser Lys Pro Leu Phe Gly Glu

His Tyr Val Arg Val Lys Ser Tyr Cys Asn Asp Gln

Ser Thr Gly Thr Leu Glu Ile Val Ser Glu Asp Leu

Ser Cys Leu Lys Gly Lys His Val Leu Ile Val Glu

Asp Ile Ile Asp Thr Gly Lys Thr Leu Val Lys Phe

Cys Glu Tyr Leu Lys Lys Phe Glu Ile Lys Thr Val

Ala Ile Ala Cys Leu Phe Ile Lys Arg Thr Pro Leu

-continued

```
Trp Asn Gly Phe Lys Ala Asp Phe Val Gly Phe Ser

Ile Pro Asp His Phe Val Val Gly Tyr Ser Leu Asp

Tyr Asn Glu Ile Phe Arg Asp Leu Asp His Cys Cys

Leu Val Asn Asp Glu Gly Lys Lys Lys Tyr Lys Ala

Thr Ser Leu
```

This sequence, and any deletions, insertions or additions which may be made within the sequence without substantially altering the activity of the HGPRT enzyme, is within the scope and protection of the present invention.

The bacterial strain used for expression of *P. falciparum* HGPRT according to the present invention was *E. coli* strain GP120 [purE Δ (lac pro gpt)] [see Biochem Biophys. Acta. 53:166 (1961)] obtained from the author. Bacterial cultures containing recombinant plasmids were routinely grown in 2XYT broth containing 100 μg/ml ampicillin. Selective plates used for assaying HGPRT expression contained M9 salts, 20 μg/ml guanine, 1 mM proline, 100 μg/ml ampicillin, 1 mM lPTG, and 2% agar.

Plasmid p1A7, containing the 1250 bp *P. falciparum* HGPRT cDNA fragment was linearized at its unique EcoR1 site and digested with Bal31 nuclease [see Experiments with Gene Fusion, Cold Spring Harbor Laboratory Press, New York, pages 205–207, (1984)] in order to delete the 500 bp of noncoding upstream sequence to a region near the HGPRT initiation codon according to the present invention as schematically depicted in FIG. 2. The resulting HGPRT cDNA was isolated and subcloned into the expression vector ptac-85 [see Nucl. Acids Res.14:3603 (1986)].

The ligated DNA molecule was transformed into *E. coli* strain GP120 [see Biochem Biophys. Acta. 53:166 (1961)] which lacks the ability to synthesize purines de novo and the ability to utilize guanine as a sole source of purine in minimal growth medium due to the absence of bacterial enzyme, guanine phosphoribosyltransferase. Only cells containing a plasmid that expresses a functional HGPRT protein which complements the gpt mutation of strain GR120 are able to grow on minimal plates containing guanine. Three isolates (pRD1, 14, and 25) were found by sequence analysis to have deletion endpoints 45 bp upstream of the HGPRT initiation codon. Plasmid pRD1 was linearized with EcoR1 and digested with Bal31 using known techniques [see Experiments in Gene Fusion, supra]. The nuclease-treated plasmid DNA was repaired with Klenow enzyme and T4 DNA polymerase to ensure the presence of blunt ends and then digested with HindIII in order to isolate and subsequently clone the HGPRT cDNA into a plasmid vector. The resulting 800 bp HGPRT insert DNA was ligated to pBS(+) vector DNA that had been digested with Xba1, repaired with Klenow enzyme, and finally digested with HindIII. The ligated DNA was used to transform *E. coli* strain JM109 (available from Stratagen) and recombinant plasmids were isolated by a "miniprep" procedure [see Molecular Cloning. A laboratory manual. Cold Spring Harbor Laboratory Press, Cold Spring Harbor, N.Y., pgs 326–328 (1982)]. Miniprep DNA samples were analyzed by digestion with Xba1, since BAL31 truncated insert fragments terminating in an A:T based pair when fused to the repaired Xba1 site of pBS (+) would regenerate the Xba1 site. Plasmids pRD189 and pRD206 were found to contain HGPRT inserts having a unique Xba1 site. Nucleotide sequence determination of these isolates demonstrated that both of these isolates terminate at an A:T pair 5 bp upstream of the *P. falciparum* HGPRT initiation codon, which allowed the HGPRT sequence to be isolated as an Xbal-Hind III fragment for subsequent cloning into an expression vector. DNA from the isolated pRD206 was digested with Xbal and HindIII and the resulting HGPRT coding sequence was isolated. The HGPRT insert DNA was made blunt ended with the single-strand specific mung bean nuclease and ligated to the expression vector ptac-85 that had been digested with BamHl and treated with mung bean nuclease. The ptac-85 expression vector contains the strong inducible tac promoter which is regulated by the gratuitous inducer lPTG to direct transcription and a lacz Shine/Dalgarno (S/D) sequence separated by 10 bps from an initiator codon, ATG, to mediate translation initiation. Generally 5–9 nucleotides are preferred between the ribosome binding site (RBS) and the ATG codon, the number determining the maximum expression of protein in ptac-85. Transformation of *E. coli* JM109 with the ligated DNA resulted in the isolation of plasmid pRD336 containing the *P. falciparum* HGPRT insert according to the present invention in the correct orientation relative to the tac promoter of ptac-85. Nucleotide sequence analysis of the junction between the Shine/Dalgarno sequence (S/D) of the ptac-85 vector and the 5' end of the *P. falciparum* HGPRT gene in plasmid pRD336 indicated that the S/D-ATG initiation codon spacing was 4 bp, whereas a spacing of generally 5–9 bp has been shown to be optimal for the expression of foreign proteins in *E. coli* [see *Microbiol*. Rev. 47:1 (1983)]. In order to isolate cDNA containing an optimal S/D-ATG spacing we chose S1 nuclease to blunt both ptac-85 vector DNA as well as the HGPRT insert cDNA from pRD206. Ligation and transformation of these S1-treated DNAs resulted in the isolation of plasmid pRD500, which sequence analysis indicated contained a S/D-ATG spacing of 9 bp. The spacing between the rbs and ATG in clone pRD336 was only 3 bp whereas the spacing in clone pRD500 was 8 bp as depicted in the following table in which the ribosome binding site is underlined:

TABLE 1

| RBS-HGPRT cDNA JUNCTION SEQUENCES | | |
|---|---|---|
| pRD336 | 5'--->3' | TTTCACAC<u>AGGA</u>AAC ATG... |
| pRD500 | 5'--->3' | TTTCACAC<u>AGGA</u>AACAGAAA ATG... |

EXAMPLE 2

Bacterial Expression of *Plasmodium falciparum* HGPRT

Bacterial cells (GP120' pRD500) were centrifuged for 10 min, 1000×g at 4° C. and washed with cold PBS. The cell pellet was stored at −70° C. until needed; the cell pellet was sonicated in 0.3 ml of a buffer composed of 25 mM Tris pH 7.5, 1 mM $MgCl_2$, 1 mM phospho-ribose-pyrophosphate (PRPP) and 3 μg each of several protease inhibitors, including leupeptin, antipain, chymostatin, pepstatin and phosphoramidone. The supernatant fraction resulting from centrifugation at 100,000×g for 30 min centrifugation served as the enzyme source for all subsequent studied, The samples were analyzed by sodium dodecyl sulfate/polyacrylamide gel electrophoresis (SDS-Page) using 15% acrylamide in slab gels and stained with Coomassie Brillant blue R250 as described previously [Laemmli, U.K.: Cleavage of structural proteins during the assembly of the head of bacteriophage T4. Nature (London) 227 (1970) 680–685.

The cDNA clone from *P. falciparum* according to the present invention is revealed to be 12 amino acids longer than human HGPRT [see Proc. Natl. Acad. Sci. USA 80:477 (1983)] and also only about 48–49 percent of the amino acids are conserved. It is also noteworthy that in the *P.* falciparum enzyme according to the present invention, only 75 percent of the amino acids are conserved in the putative residue catalytic domain. These differences may be the reason that the parasite HGPRT is able to utilize xanthine as a substrate but the human HGPRT is not. It is this utilization which makes the HGPRT according to the present invention a potential target for chemotherapeutic attack. Since the parasite HGPRT can use xanthine as a substrate, it is reasonable to believe that xanthine analogues or related compounds should inhibit the parasitic enzyme while the human HGPRT enzyme will not be inhibited by these same analogues or compounds. Thus, as stated earlier, the inhibition of the parasite HGPRT should effectively suppress the parasite's growth and development while allowing for pharmaceutical therapies and the host immune responses to combat the infection.

Thus, while we have illustrated and described the preferred embodiment of our invention, it is to be understood that this invention is capable of variation and modification and we therefore do not wish or intend ourselves to be limited to the precise terms set forth, but desire to avail ourselves of such changes and alterations which may be made for adapting the invention to various usages and conditions. Accordingly, such changes and alterations are properly intended to be within the full range of equivalents, and therefore within the purview of the following claims.

Having thus described our invention and the manner and a process of making and using it in such clear, full, concise and exact terms so as to enable any person skilled in the art to which it pertains, or with which it is mostly nearly connected, to make and use the same;

We claim:

1. An isolated and purified dimeric protein having a molecular weight of about 52,000 daltons and having substantially the following amino acid residue sequence:

```
Met Pro Ile Pro Asn Asn Pro Gly Ala Gly Glu Asn
Ala Phe Asp Pro Val Phe Val Lys Asp Asp Asp Gly
Tyr Asp Leu Asp Ser Phe Met Ile Pro Ala His Tyr
Lys Lys Tyr Leu Thr Lys Val Leu Val Pro Asn Gly
Val Ile Lys Asn Arg Ile Glu Lys Leu Ala Tyr Asp
Ile Lys Lys Val Tyr Asn Asn Glu Glu Phe His Ile
Leu Cys Leu Leu Lys Gly Ser Arg Gly Phe Phe Thr
Ala Leu Leu Lys His Leu Ser Arg Ile His Asn Tyr
Ser Ala Val Glu Thr Ser Lys Pro Leu Phe Gly Glu
His Tyr Val Arg Val Lys Ser Tyr Cys Asn Asp Gln
Ser Thr Gly Thr Leu Glu Ile Val Ser Glu Asp Leu
Ser Cys Leu Lys Gly Lys His Val Leu Ile Val Glu
Asp Ile Ile Asp Thr Gly Lys Thr Leu Val Lys Phe
Cys Glu Tyr Leu Lys Lys Phe Glu Ile Lys Thr Val
Ala Ile Ala Cys Leu Phe Ile Lys Arg Thr Pro Leu
Trp Asn Gly Phe Lys Ala Asp Phe Val Gly Phe Ser
Ile Pro Asp His Phe Val Val Gly Tyr Ser Leu Asp
Tyr Asn Glu Ile Phe Arg Asp Leu Asp His Cys Cys
```

-continued

```
Leu Val Asn Asp Glu Gly Lys Lys Lys Tyr Lys Ala
Thr Ser Leu.
```

2. A cDNA sequence encoding for *Plasmodium falciparum* HGPRT.

3. A purified isolated DNA sequence consisting essentially of a DNA sequence coding for the protein having the amino acid residue sequence according to claim 1 or for a protein having having substantially the same amino acid sequence and substantially the same HGPRT activity as the protein defined in claim 1.

4. A purified isolated DNA sequence according to claim 3 wherein one such sequence is:

```
ATG CCA ATA CCA AAT AAT CCA GGA GCT GGT GAA AAT
CCC TTT GAT CCC GTT TTC GTA AAG GAT GAC GAT GGT
TAT GAC CTT GAT TCT TTT ATG ATC CCT GCA CAT TAT
AAA AAA TAT CTT ACC AAG GTC TTA GTT CCA AAT GGT
GTC ATA AAA AAC CGT ATT GAG AAA TTG GCT TAT GAT
ATT AAA AAG GTG TAC AAC AAT GAA GAG TTT CAT ATT
CTT TGT TTG TTG AAA GGT TCT CGT GGT TTT TTC ACT
GCT CTC TTA AAG CAT TTA AGT AGA ATA CAT AAT TAT
AGT GCC GTT GAG ACG TCC AAA CCA TTA TTT GGA GAA
CAC TAC GTA CGT GTG AAA TCC TAT TGT AAT GAC CAA
TCA ACA GGT ACA TTA GAA ATT GTA AGT GAA GAT TTA
TCT TGT TTA AAA GGA AAA CAT GTA TTA ATT GTT GAA
GAT ATT ATT GAT ACT GGT AAA ACA TTA GTA AAG TTT
TGT GAA TAC TTA AAG AAA TTT GAA ATA AAA ACC GTT
GCC ATC GCT TGT CTT TTT ATT AAA AGA ACA CCT TTG
TGG AAT GGT TTT AAA GCT GAT TTC GTT GGA TTC TCA
ATT CCT GAT CAC TTT GTT GTT GGT TAT AGT TTA GAC
TAT AAT GAA ATT TTC AGA GAT CTT GAC CAT TGT TGT
TTG GTT AAT GAT GAG GGA AAA AAG AAA TAT AAA GCA
ACT TCA TTA TAA.
```

5. An isolated and purified protein which is *Plasmodium falciparum* HGPRT enzyme.

6. An expression vector comprising a DNA sequence encoding for an enzyme selected from the group consisiting of (1) *P. falciparum* HGPRT enzyme; and (2) a HGPRT active mutant of *P. falciparum* HGPRT enzyme or a fragment thereof having substantially the same activity as the enzyme wherein an amino acid residue has been inserted, substituted or deleted in or from the amino acid sequence of the enzyme or its fragment.

7. A purified protein isolated from a recombinant organism transformed with a vector that codes for the expression of *Plasmodium falciparum* HGPRT said protein having having substantially the same amino acid sequence and substantially the same HGPRT activity as the protein according to claim 1.

* * * * *

UNITED STATES PATENT AND TRADEMARK OFFICE
CERTIFICATE OF CORRECTION

PATENT NO.   : 6,248,577 B1
DATED        : June 19, 2001
INVENTOR(S)  : Vasanthakumar et al.

It is certified that error appears in the above-identified patent and that said Letters Patent is hereby corrected as shown below:

<u>Claim 7,</u>
Line 61, change "having having" to read -- having --.

Signed and Sealed this

Twenty-ninth Day of January, 2002

*Attest:*

*Attesting Officer*

JAMES E. ROGAN
*Director of the United States Patent and Trademark Office*